United States Patent [19]
Falling et al.

[11] Patent Number: 5,710,289
[45] Date of Patent: Jan. 20, 1998

[54] PROCESS FOR THE PREPARATION OF DIHALOTETRAHYDROFURANS FROM DIHYDROFURAN

[75] Inventors: Stephen N. Falling; Patricia Lopez, both of Kingsport,, Tenn.

[73] Assignee: Eastman Chemical Company, Kingsport,, Tenn.

[21] Appl. No.: 779,758

[22] Filed: Jan. 7, 1997

[51] Int. Cl.$^6$ .................................. C07D 307/56
[52] U.S. Cl. .................................. 549/504
[58] Field of Search .................................. 549/504

[56] References Cited

U.S. PATENT DOCUMENTS 5,103,028   4/1992   Falling et al. .................... 549/540

FOREIGN PATENT DOCUMENTS 616762   1/1949   United Kingdom .

OTHER PUBLICATIONS

L. Crombie, et al., J. Chem. Soc., 136 (1956).
A. Nersasian, I. Eng. Chem. Prod. Res. Dev., 2 138 (1963).
W. Reppe, et al., Annalen., 596, 1, 138 (1955).
H. R. Buys, et al., Tetrahedron, 24, 3019 (1968).
R. Paul, et al., Mémoires Présentés a la Société Chimique, 669 (1950).
S. Olsen, Acta Chem. Sand., 4, 473 (1950).
Crombie, et al., J. Chem. Soc., Perkin Trans. 1, 1971 (1985).
Pezechk et al., Tetrahedron Letters, vol.27, No. 32, pp. 3715–3718, 1986.

*Primary Examiner*—Bernard Dentz
*Attorney, Agent, or Firm*—J. Frederick Thomsen; Harry J. Gwinnell

[57] ABSTRACT

Disclosed is a process for the preparation of 3,4-dichlorotetrahydrofuran, 3,4-dibromotetrahydrofuran, 2,3-dichlorotetrahydrofuran, and 2,3-dibromotetrahydrofuran by the reaction of 2,5- or 2,3-dihydrofuran with chlorine or bromine in the presence of a quaternary onium halide compound. The reaction preferably is carried out by the addition of the dihydrofuran and chlorine or bromine to an organic, halogenation solvent containing chlorine or bromine and the quaternary onium halide compound.

13 Claims, No Drawings

PROCESS FOR THE PREPARATION OF DIHALOTETRAHYDROFURANS FROM DIHYDROFURAN

This invention pertains to the preparation of dihalotetrahydrofurans by the reaction of chlorine or bromine with dihydrofurans. More specifically, this invention pertains to the chlorination or bromination of dihydrofurans in the presence of an inert solvent and an onium halide.

Dihalotetrahydrofurans, particularly 2,3-dichlorotetrahydrofuran and 2,3-dibromotetrahydrofuran, are valuable compounds useful as intermediates in the synthesis of a wide variety of products. See, for example, the uses described by L. Crombie, et al., *J. Chem. Soc.*, 136 (1956), A. Nersasian, *I. Eng. Chem. Prod. Res. Dev.*, 2 138 (1963) and the references cited therein.

W. Reppe, et al., *Annalen.*, 596, 1, 138 (1955) have reported the preparation of 3,4-dichlorotetrahydrofuran by chlorination of 2,5-dihydrofuran at a temperature below 10° C. followed by distillation at 59°–61° C. at 14 torr. The chlorination in acetic acid to give 3,4-dichlorotetrahydrofuran and 3-chloro-4-acetoxytetrahydrofuran is disclosed in British Patent 616, 762; *Chem. Abstr.*, 43, 5425a (1949). H. R. Buys, et al., *Tetrahedron*, 24, 3019 (1968) describe the chlorination of 2,5-dihydrofuran using sulfuryl chloride. The bromination of 2,5-dihydrofuran to give 3,4-dibromotetrahydrofuran has been reported in papers by H. R. Buys, et al., *Tetrahedron*, 24, 3019 (1968), R. Paul, et al., *Mémoires Présentés a la Société Chimique*, 669 (1950) and S. Olsen, *Acta Chem. Scand.*, 4, 473 (1950). W. Reppe, et al., ibid, also describes the preparation of 2,3-dichlorotetrahydrofuran by reaction of tetrahydrofuran with chlorine gas. L. Crombie, et al., ibid, have reported the preparation of 2,3-dichlorotetrahydrofuran by chlorination of 2,3-dihydrofuran or tetrahydrofuran with dry chlorine. A. Nersasian, ibid, prepared 2,3-dichlorotetrahydrofuran from tetrahydrofuran with sulfuryl chloride. Similar procedures, as well as the bromination of 2,3-dihydrofuran to 2,3-dibromotetrahydrofuran, have been published by Crombie, et al., *J. Chem. Soc., Perkin Trans.* 1, 1971 (1985).

The chlorination of 2,5-dihydrofuran according to a conventional halogenation procedure wherein a slight stoichiometric excess of chlorine was added to a 13% solution of 2,5-dihydrofuran in dichloromethane at −5° to 5° C. produced 3,4-dichlorotetrahydrofuran. However, about 22% of the 2,5-dihydrofuran was converted to high-boiling, oligomeric compounds. Distillation of the product away from the by-products was not possible. Gas chromatographic assay of the crude product showed only 78% of 3,4-dichlorotetrahydrofuran.

We have discovered that dihalotetrahydrofurans may be conveniently prepared in good yields and high purity by the reaction of dihydrofuran and chlorine or bromine in the presence of a quaternary onium halide. The present invention therefore provides a process for the preparation of a dihalotetrahydrofuran which comprises reacting a dihydrofuran with $X_2$ in the presence of a quaternary onium halide compound; wherein the dihalotetrahydrofuran is 3,4-dichlorotetrahydrofuran, 3,4-dibromotetrahydrofuran, 2,3-dichlorotetrahydrofuran, or 2,3-dibromotetrahydrofuran; the dihydrofuran is 2,5- or 2,3-dihydrofuran; and $X_2$ is chlorine or bromine. The process may be carried out in the presence of a conventional halogenation solvent.

The quaternary onium halide compound used in the process may be selected from a wide variety of tetrasubstituted ammonium, phosphonium and arsonium compounds. Numerous examples of both types of onium compounds and specific onium compounds are described in U.S. Pat. No. 5,082,956. The preferred onium halides are tetrahydrocarbylammonium and tetrahydrocarbylphosphonium halides having the formula:

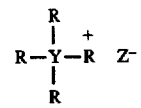

wherein each R is a hydrocarbyl group; Y is a nitrogen or phosphorus atom; $Z^{31}$ is a halide such as $Cl^-$, $Br^-$ and $I^-$.

The tetrahydrocarbylammonium and tetrahydrocarbylphosphonium halide compounds may contain a total of 4 to about 60 carbon atoms, preferably about 8 to 32 carbon atoms, provided, of course, that the onium halide compound exhibits sufficient solubility in the particular halogenation solvent used. When using one of the preferred halogenation solvents such as a chlorinated hydrocarbon, the onium halides which are particularly preferred are the tetran-butylphosphonium halides and the tetraethylammonium halides. These specific onium halides are sufficiently soluble in the preferred halogenation solvents to enable their use in catalytically-effective amounts and are sufficiently water soluble to permit their removal by water washing the dihalotetrahydrofuran product. However, it may be possible to utilize the dihalotetrahydrofuran product without the removal of the onium halide catalyst. The halide anion $Z^-$ of the onium halides normally is the same as in the halogen $X_2$ used in the process. The catalytically-effective amount of the onium halide compound typically is in the range of about 0.001 to 0.1 moles per liter of halogenation solvent.

The organic, halogenation solvent normally used in the process of the present invention may be selected from various aliphatic, cycloaliphatic and aromatic hydrocarbons and halogenated derivatives thereof. Halogenated hydrocarbons, such as chlorinated alkanes and halobenzenes, e.g., dichloromethane, chloroform, carbon tetrachloride, 1,2-dichloroethane, tetrachloro-ethylene, 1,1,1-trichloroethane, 4-chlorobenzotri-fluoride, 3,4-dichlorobenzotrifluoride, chlorobenzene and the isomers of di- and tri-chlorobenzene, are preferred since non-halogenated hydrocarbons may result in product of lower quality and/or halogenation of the solvent during the process. The use of catalyst/solvent combinations comprising (1) tetran-butylphosphonium chloride or bromide with 4-chlorobenzotrifluoride, chlorobenzene or dichloromethane and (2) tetraethyl-ammonium chloride or bromide with 4-chlorobenzotri-fluoride or dichloromethane are particularly preferred.

The halogenation process in general may be carried out at a temperature of about −20° to 70° C. When a dihydrofuran is chlorinated according to our invention, a reaction temperature of about −10° to 20° C. is preferred whereas a range of about 0 ° to 50° C. is preferred for bromination.

Best results are achieved when the chlorine or bromine reactant is maintained in excess relative to the dihydrofuran during essentially all of the process. Thus, a preferred embodiment of the present invention concerns the addition of a dihydrofuran to a solution of chlorine or bromine and a quaternary ammonium or phosphonium halide, preferably chloride or bromide, in an organic, halogenation solvent. At the commencement of the operation of the process, the halogenation solvent contains dissolved chlorine or bromine and then chlorine or bromine and the dihydrofuran are added at rates or in increments which maintain dissolved chlorine or bromine in the reaction mixture. At the end of a production run or batch, the addition of chlorine is stopped and dihydrofuran may be added to consume all of the dissolved chlorine or bromine or unreacted halogen may be removed by distillation or by washing with an aqueous reducing agent such as sodium thiosulfate.

The preferred embodiment described hereinabove comprises a process for the preparation of a dihalotetrahydrofuran compound which comprises adding a dihydrofuran and $X_2$ to a solution of $X_2$ and a quaternary nitrogen or phosphorus onium halide compound having the formula

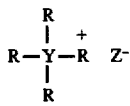

in an organic, halogenation solvent, wherein each R is a hydrocarbyl group; Y is a nitrogen or phosphorus atom; and $X^-$ is $Cl^-$ or $Br^-$; wherein the dihalotetrahydrofuran is 3,4-dichlorotetrahydrofuran, 3,4-dibromotetrahydrofuran, 2,3-dichlorotetrahydrofuran, or 2,3-dibromotetrahydrofuran; the dihydrofuran is 2,5- or 2,3-dihydrofuran; and $X_2$ is chlorine or bromine. The use of 2,5-dihydrofuran to produce 3,4-dichlorotetrahydrofuran or 3,4-dibromotetrahydrofuran is particularly preferred. As mentioned above, the dihydrofuran and halogen $X_2$ may be added simultaneously or intermittently and/or separately to maintain dissolved halogen in the reaction during most of the process time. The presence of dissolved halogen is evident from the color of the reaction mixture; a light green for chlorine and orange for bromine. At the conclusion of the process, the mixture is given an aqueous work-up to remove catalyst and excess halogen.

The halogenation process of the present invention is further illustrated by the following examples. Gas chromatographic (GC) analyses (reported in area-percent) were performed on a Hewlett-Packard 5890A gas chromatograph with a 30 meter DB-5 0.32 mm inside diameter capillary column with a 0.25 micron film thickness. The temperature program was 35° C. (4.5 minutes), 20° C. per minute to 280° C., hold 5 minutes. The structures of the products obtained were confirmed by nuclear magnetic resonance and mass spectrometry.

EXAMPLE 1

A 500-mL, four-neck, round-bottom flask was equipped with a gas addition tube, thermocouple, mechanical stirrer, condenser, addition funnel (for the 2,5-dihydrofuran), and a cooling bath. To the flask were added 1.0 g (6.0 mmoles) of tetraethylammonium chloride and 200 mL of dichloromethane. The solution was cooled to −5° to 5° C. then the chlorine gas addition was begun. After the solution had turned light green, 2,5-dihydrofuran and chlorine were added simultaneously over about one hour at −5° to 5° C. A total of 38 mL (0.50 moles) 2,5-dihydrofuran was added dropwise and the chlorine addition was controlled so as to keep the reaction solution green in color. After all the 2,5-dihydrofuran had been added and the chlorine addition was stopped, the solution had a light green color. A total of 40 g (0.56 moles) of chlorine was added to the mixture. The mixture was washed once with 100 mL of a 10% aqueous solution of sodium thiosulfate, twice with 100 mL of distilled water, and once with 100 mL of aqueous sodium bicarbonate (50 mL of water and 50 mL of saturated aqueous sodium bicarbonate). The mixture was dried with anhydrous magnesium sulfate, filtered, and the solvent removed from the filtrate by vacuum rotary evaporation (up to 35° C. and about 30 torr). The crude yellow product (77.2 g) was vacuum distilled at 10 torr to give trans-3,4-dichlorotetrahydrofuran at 49°–50° C. The light yellow product weighed 56.4 g (theory 71.4 g, 78.9%) and had a GC assay of 99.0%.

EXAMPLE 2

A 500-mL, four-neck, round-bottom flask was equipped with a thermocouple, a mechanical stirrer, a condenser, a liquid feed pump (for the 2,5-dihydrofuran), an addition funnel (for the bromine), and a cooling bath. To the flask were added 200 mL of dichloromethane, 1.0 g (4.8 mmoles) of tetraethylammonium bromide and a few drops of bromine. To the orange solution were added 38 mL (0.50 moles) of 2,5-dihydrofuran and 26 mL (0.488 moles) of bromine. The 2,5-dihydrofuran was pumped into the flask at a rate of 2.4 mL/minute and the bromine addition rate was controlled so as to keep the reaction solution orange in color. The solution temperature was held at 26°–40° C. during the additions. The final mixture was washed once with 100 mL of a 10% solution of aqueous sodium thiosulfate, once with 100 mL of distilled water, and once with 100 mL of aqueous sodium bicarbonate (50 mL of water plus 50 mL saturated aqueous sodium bicarbonate). The mixture was dried with anhydrous magnesium sulfate, filtered, and the solvent removed from the filtrate by vacuum rotary evaporation (up to 35° C. and about 30 torr). The crude yellow product was vacuum distilled at 9.0 torr to give trans-3,4-dibromotetrahydrofuran at 77°–81° C. The light yellow product weighed 83.8 g (theory 114.8 g, 73.0%) and had a GC assay of 99.7%.

EXAMPLE 3

A 500-mL, four-neck, round-bottom flask was equipped with a thermocouple, a mechanical stirrer, a condenser, two addition funnels, and a cooling bath. To the flask were added 200 mL of dichloromethane, 1.0 g (4.8 mmoles) of tetraethylammonium bromide and a few drops of bromine. To the orange solution were added 38 mL (0.50 moles) of 2,3-dihydrofuran and 26 mL (0.488 moles) of bromine. The 2,3-dihydrofuran was added dropwise to the orange solution over approximately 45 minutes and the bromine was added at a rate so as to keep the reaction solution orange in color. The solution temperature was held at 0°–5° C. during the additions. After the additions were complete, about 2 mL of 2,3-dihydrofuran was added to decolorize the solution before allowing it to warm to room temperature. GC analysis of the solution showed (disregarding solvent) 91.2% 2,3-dibromotetrahydrofuran. NMR of a concentrated sample was consistent with that expected for trans-2,3-dibromotetrahydrofuran.

COMPARATIVE EXAMPLE 1

This example illustrates the results obtained when no onium halide compound is used and chlorine is added to a solution of 2,5-dihydrofuran in a halogenation solvent in the chlorination of 2,5-dihydrofuran. A 500-mL, four-neck, round-bottom flask was equipped with a gas addition tube, thermocouple, mechanical stirrer, condenser, and a cooling bath. To the flask were added 35.2 g (0.502 moles) of 2,5-dihydrofuran and 200 mL of dichloromethane. The solution was cooled to −5° to 5° C. then the addition of chlorine gas was begun. Chlorine (41.9 g, 0.591 moles) was added at −5° to 5° C. until the solution turned green and remained green for a while. At this time the GC showed no 2,5-dihydrofuran so the chlorine addition was stopped. The mixture was washed once with 100 mL of a 10% aqueous solution of sodium thiosulfate, twice with 100 mL of distilled water, and once with 100 mL of aqueous sodium bicarbonate (50 mL of water plus 50 mL saturated aqueous sodium bicarbonate). The mixture was dried with anhydrous magnesium sulfate, filtered, and the solvent was removed from the filtrate by vacuum rotary evaporation (up to 35° C. and about 30 torr). The crude yellow product weighed 92.8 g (theory 70.4 g) and assayed 78.4% by gas chromatography. Purification by distillation was unsuccessful due to high boiling contaminants.

COMPARATIVE EXAMPLE 2

This example illustrates the results obtained when no onium halide compound is used and bromine is added to a solution of 2,5-dihydrofuran in a halogenation solvent in the bromination of 2,5-dihydrofuran.

A 500-mL, four-neck, round-bottom flask was equipped with a thermocouple, a mechanical stirrer, a condenser, an addition funnel, and a cooling bath. To the flask were added 200 mL of dichloromethane and 38 mL (0.50 moles) of 2,5-dihydrofuran. A total of 26 mL (0.488 moles) of bromine was added to the mixture. The solution was held at 26°–40° C. during the bromine addition. The bromine addition was controlled so as to keep the reaction solution orange in color. At the beginning of the addition the bromine color disappears rapidly indicating a fast reaction. Half-way through the bromine addition, the orange color changed to light green then finally dark blue. The mixture was washed once with 100 mL of a 10% solution of aqueous sodium thiosulfate, once with 100 mL of distilled water, and once with 100 mL of aqueous sodium bicarbonate (50 mL of water plus 50 mL saturated aqueous sodium bicarbonate). After the sodium thiosulfate wash, the hazy solution turned a light amber in color. The mixture was dried with anhydrous magnesium sulfate, filtered, and the solvent was removed from the filtrate by vacuum rotary evaporation (up to 30° C. and about 30 torr). The crude, amber product weighed 96.5 g (theory 114.8 g). A GC analysis of the crude material showed the following results: 2.9% 2,5-dihydrofuran, 16.6% dichloromethane, 5.1% low boilers, 64.3% 3,4-dibromotetrahydrofuran, and 11.1% high boilers. No distillation was performed because the material was very unstable (turned black and deposited solids).

COMPARATIVE EXAMPLE 3

This example illustrates the results obtained when no onium halide compound is used and bromine is added to a solution of 2,5-dihydrofuran in a halogenation solvent in the bromination of 2,5-dihydrofuran while maintaining the reaction temperature at 5°–10° C.

A 500-mL, four-neck, round-bottom flask was equipped with a thermocouple, a mechanical stirrer, a condenser, an addition funnel, and a cooling bath. To the flask were added 200 mL of dichloromethane and 38 mL (0.50 moles) of 2,5-dihydrofuran. A total of 26 mL (0.488 moles) of bromine was added to the mixture. The solution was kept around 5°–10° C. during the bromine addition. The bromine addition was controlled so as to keep the reaction solution orange in color. At the beginning of the addition the bromine color disappears rapidly indicating a fast reaction. After the bromine addition was finished the mixture turned light green and then blue. The mixture was washed once with 50 mL of a 10% solution of aqueous sodium thiosulfate, once with 50 mL of distilled water, and once with 50 mL of aqueous sodium bicarbonate (25 mL of water plus 25 mL saturated aqueous sodium bicarbonate). After the sodium thiosulfate wash the solution turned a light orange color. The mixture was dried with anhydrous magnesium sulfate, filtered, and the solvent was removed from the filtrate by vacuum rotary evaporation (up to 30° C. and about 30 torr). GC analysis of the crude material showed the following results: 21.3% low boilers, 7.6% high boilers, and 71.1% 3,4-dibromotetrahydrofuran. The sample color after filtering was black, and no further distillation was attempted.

The invention has been described in detail with particular reference to preferred embodiments thereof, but it will be understood that variations and modifications can be effected within the spirit and scope of the invention.

We claim:

1. Process for the preparation of a dihalotetrahydrofuran which comprises reacting a dihydrofuran with $X_2$ in the presence of a quaternary onium halide compound; wherein the dihalotetrahydrofuran is 3,4-dichlorotetrahydrofuran, 3,4-dibromotetrahydrofuran, 2,3-dichlorotetrahydrofuran, or 2,3-dibromotetrahydrofuran; the dihydrofuran is 2,5- or 2,3-dihydrofuran; and $X_2$ is chlorine or bromine.

2. Process according to claim 1 wherein the quaternary onium halide has the formula

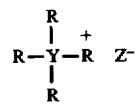

wherein each R is a hydrocarbyl group; Y is a nitrogen or phosphorus atom; $Z^-$ is a halide.

3. Process according to claim 1 for the preparation of a dichlorotetrahydrofuran which comprises reacting a dihydrofuran and $Cl_2$ at a temperature of about −10° to 20° C. in the presence of a quaternary nitrogen or phosphorus onium chloride compound containing a total of about 8 to 32 carbon atoms and having the formula

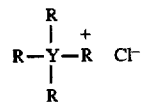

and an organic, halogenation solvent; wherein each R is a hydrocarbyl group, Y is a nitrogen or phosphorus atom; the dichlorotetrahydrofuran is 3,4-dichlorotetrahydrofuran or 2,3-dichlorotetrahydrofuran, and the dihydrofuran is 2,5- or 2,3-dihydrofuran.

4. Process according to claim 3 wherein the onium chloride is tetra-n-butylphosphonium chloride or tetraethylammonium hloride and the solvent is 4-chlorobenzotrifluoride, chlorobenzene or dichloromethane.

5. Process according to claim 3 wherein the onium chloride is tetra-n-butylphosphonium chloride or tetraethylammonium chloride and the solvent is 4-chlorobenzotrifluoride, chlorobenzene or dichloromethane, the dichlorotetrahydrofuran is 3,4-dichlorotetrahydrofuran and the dihydrofuran is 2,5-dihydrofuran.

6. Process according to claim 1 for the preparation of a dibromotetrahydrofuran which comprises reacting a dihydrofuran and $Br_2$ at a temperature of about 0° to 50° C. in the presence of a quaternary nitrogen or phosphorus onium bromide compound containing a total of about 8 to 32 carbon atoms and having the formula

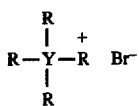

and an organic, halogenation solvent; wherein each R is a hydrocarbyl group and Y is a nitrogen or phosphorus atom; the dibromotetrahydrofuran is 3,4-dibromotetrahydrofuran or 2,3-dibromotetrahydrofuran, and the dihydrofuran is 2,5- or 2,3-dihydrofuran.

7. Process according to claim 6 wherein the onium bromide is tetra-n-butylphosphonium bromide or tetraethylammonium bromide and the solvent is 4-chlorobenzotrifluoride, chlorobenzene or dichloromethane.

8. Process according to claim 6 wherein the onium bromide is tetra-n-butylphosphonium bromide or tetraethylammonium bromide and the solvent is 4-chlorobenzotrifluoride, chlorobenzene or dichloromethane, the dibromotetrahydrofuran is 3,4-dibromotetrahydrofuran and the dihydrofuran is 2,5-dihydrofuran.

9. Process for the preparation of a dihalotetrahydrofuran which comprises adding a dihydrofuran and $X_2$ to a solution of $X_2$ and a quaternary onium halide in an organic, halogenation solvent; wherein the dihalotetrahydrofuran is 3,4-dichlorotetrahydrofuran, 3,4-dibromotetrahydrofuran, 2,3-dichlorotetrahydrofuran, or 2,3-dibromotetrahydrofuran; the dihydrofuran is 2,5- or 2,3-dihydrofuran; and $X_2$ is chlorine or bromine.

10. Process according to claim 9 for the preparation of a dichlorotetrahydrofuran compound which comprises adding a dihydrofuran and $Cl_2$ to a solution of $Cl_2$ and a quaternary nitrogen or phosphorus onium chloride compound containing a total of about 8 to 32 carbon atoms and having the formula

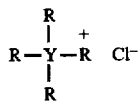

in an organic, halogenation solvent at a temperature of about −10° to 20° C., wherein each R is a hydrocarbyl group, Y is a nitrogen or phosphorus atom, the dichlorotetrahydrofuran is 3,4-dichlorotetrahydrofuran or 2,3-dichlorotetrahydrofuran, and the dihydrofuran is 2,5- or 2,3-dihydrofuran.

11. Process according to claim 10 wherein the onium chloride is tetra-n-butylphosphonium chloride or tetraethylammonium chloride, the solvent is 4-chlorobenzotrifluoride, chlorobenzene or dichloromethane, the dichlorotetrahydrofuran is 3,4-dichlorotetrahydrofuran and the dihydrofuran is 2,5-dihydrofuran.

12. Process according to claim 9 for the preparation of a dibromotetrahydrofuran compound which comprises adding a dihydrofuran and $Br_2$ to a solution of $Br_2$ and a quaternary nitrogen or phosphorus onium bromide compound containing a total of about 8 to 32 carbon atoms and having the formula

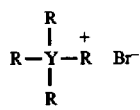

in an organic, halogenation solvent at a temperature of about 0° to 50° C., wherein each R is a hydrocarbyl group, Y is a nitrogen or phosphorus atom, the dibromotetrahydrofuran is 3,4-dibromotetrahydrofuran or 2,3-dibromotetrahydrofuran, and the dihydrofuran is 2,5- or 2,3-dihydrofuran.

13. Process according to claim 12 wherein the onium bromide is tetra-n-butylphosphonium bromide or tetraethylammonium bromide, the solvent is 4-chlorobenzotrifluoride, chlorobenzene or dichloromethane, the dibromotetrahydrofuran is 3,4-dibromotetrahydrofuran and the dihydrofuran is 2,5-dihydrofuran.

* * * * *